United States Patent
Ciok

(10) Patent No.: US 8,728,047 B2
(45) Date of Patent: May 20, 2014

(54) BODY WASTE COLLECTING DEVICE

(75) Inventor: Danuta Ciok, Nivaa (DK)

(73) Assignee: Coloplast A/S, Humlebaek (DK)

( * ) Notice: Subject to any disclaimer, the term of this patent is extended or adjusted under 35 U.S.C. 154(b) by 34 days.

(21) Appl. No.: 13/511,764

(22) PCT Filed: Nov. 26, 2010

(86) PCT No.: PCT/DK2010/050322
§ 371 (c)(1),
(2), (4) Date: May 24, 2012

(87) PCT Pub. No.: WO2011/063818
PCT Pub. Date: Jun. 3, 2011

(65) Prior Publication Data
US 2012/0283677 A1 Nov. 8, 2012

(30) Foreign Application Priority Data
Nov. 27, 2009 (DK) ................... 2009 70233

(51) Int. Cl.
*A61F 5/44* (2006.01)
(52) U.S. Cl.
USPC ......................................................... 604/336
(58) Field of Classification Search
USPC ......................................................... 604/336
See application file for complete search history.

(56) References Cited

U.S. PATENT DOCUMENTS

| | | | |
|---|---|---|---|
| 3,339,546 A * | 9/1967 | Chen .................................. | 602/56 |
| 4,231,369 A * | 11/1980 | Sorensen et al. .............. | 604/336 |
| 4,477,325 A * | 10/1984 | Osburn ........................ | 264/488 |
| 4,538,603 A | 9/1985 | Pawelchak et al. | |
| 4,551,490 A * | 11/1985 | Doyle et al. ..................... | 524/22 |
| 4,738,257 A * | 4/1988 | Meyer et al. .................... | 602/48 |
| 4,775,374 A * | 10/1988 | Cilento et al. ................ | 604/344 |
| 6,326,421 B1 * | 12/2001 | Lipman ........................... | 524/22 |
| 6,451,883 B1 | 9/2002 | Chen et al. | |
| 6,583,220 B1 * | 6/2003 | Lipman ........................ | 525/54.3 |

(Continued)

FOREIGN PATENT DOCUMENTS

| WO | WO 89/05619 | 6/1989 |
|---|---|---|
| WO | WO 00/18554 | 4/2000 |

(Continued)

*Primary Examiner* — Susan Su
*Assistant Examiner* — Guy K Townsend
(74) *Attorney, Agent, or Firm* — Coloplast Corp., Coloplast A/S; Nick Baumann

(57) ABSTRACT

The application discloses a body waste collecting device comprising a collecting pouch and an adhesive wafer for attachment to the skin, said wafer comprising a backing layer and a first and second layer of hydrocolloid adhesive, where the second layer of hydrocolloid adhesive is at least partly interposed between the first layer of hydrocolloid adhesive and the backing layer, the first and second adhesive layers consisting of a continuous phase and a discontinuous phase, wherein a) the discontinuous phase of the first adhesive layer comprises pectin, carboxymethyl cellulose, gelatine, guar gum, and potato starch,
b) the discontinuous phase of the second adhesive layer comprises carboxymethyl cellulose, gelatine, and guar gum,
c) the composition of the continuous phase of the first adhesive layer comprises a polyisobutylene, a styrene block copolymer, a butyl rubber, and a tackifier,
d) the composition of the continuous phase of the second adhesive layer consists of polyisobutylene and styrene block copolymer.

11 Claims, 1 Drawing Sheet

(56) References Cited

U.S. PATENT DOCUMENTS

| | | | |
|---|---|---|---|
| 6,710,100 B1 * | 3/2004 | Lipman | 523/111 |
| 6,840,924 B2 * | 1/2005 | Buglino et al. | 604/337 |
| 8,147,469 B2 * | 4/2012 | Nordby et al. | 604/336 |
| 8,207,393 B2 * | 6/2012 | Bach | 602/54 |
| 2002/0147265 A1 * | 10/2002 | Ding et al. | 524/501 |
| 2004/0006320 A1 * | 1/2004 | Buglino et al. | 604/344 |
| 2005/0096611 A1 * | 5/2005 | Stoyer et al. | 604/332 |
| 2008/0275327 A1 * | 11/2008 | Faarbaek et al. | 600/382 |
| 2009/0030361 A1 * | 1/2009 | Bach | 602/54 |
| 2010/0286640 A1 * | 11/2010 | Nordby et al. | 604/336 |

FOREIGN PATENT DOCUMENTS

| | | | | |
|---|---|---|---|---|
| WO | WO 01/05340 | | 1/2001 | |
| WO | WO 2007/076862 | | 7/2007 | |
| WO | WO 2007/082538 | | 7/2007 | |
| WO | WO2007082538 | * | 7/2007 | A61L 24/08 |

\* cited by examiner

BODY WASTE COLLECTING DEVICE

This is a national stage of PCT/DK10/050322 filed Nov. 26, 2010 and published in English, which claims the priority of Denmark number PA 2009 70233 filed Nov. 27, 2009, herby incorporated by reference.

FIELD OF THE INVENTION

The present invention relates to a collecting device for attachment to the skin and for collecting bodily waste, e.g. an ostomy device.

BACKGROUND OF THE INVENTION

Collecting devices for collecting bodily waste, ostomy appliances, wound or fistulae drainage bandages or devices for collecting urine are usually in the form of a receptacle, e.g. a bag, pouch or tube connected to an adhesive wafer that can be attached to the skin of the patient for receiving the waste. The wafer is typically in the form of a backing layer coated on the skin-facing surface with an adhesive layer, and the wafer may further be provided with an aperture for accommodating the body opening. The size and shape of said aperture can often be adapted individually to fit the anatomy of the patient.

One of the crucial parts of such devices is the adhesive wafer. The wafer should be able to fit leak proof around the body opening and have good adherence to the skin without unintended detachment from the skin, but at the same time the wafer should be easy to remove again without damaging the skin. Furthermore, the wafer should be able to follow the movements of the body and be comfortable to wear.

When designing a skin adhesive for the wafer, one of the major issues is to keep the skin relatively dry underneath the adhesive in order to prevent maceration. Maceration occurs when the skin is unable to get rid of moisture from transpiration and output from a body opening. This may result in degradation of the skin's barrier function as well as bad adhesion of the device to skin.

Various skin friendly hydrocolloid adhesive compositions are described in the art. Moreover, adhesive constructions comprising layers of hydrocolloid adhesives are well known in the art.

WO 2007/082538 describes a layered adhesive construction comprising at least two layers of hydrocolloid adhesives having different hydrocolloid compositions.

The layered adhesive constructions of the prior art are mainly focused on solutions for getting rid of the moisture from transpiration due to the fact that these adhesive constructions are to be applied on the human skin.

WO 89/05619 describes an adhesive skin barrier product consisting of alternating zones of material of at least two different kinds, at least one of which is a skin friendly self-adhesive material. This construction is known as a Swiss roll construction. It provides a construction where two adhesive compositions are separated. Thus, the component of each composition cannot migrate into the other composition. Migration can destroy the structure of the adhesive. Furthermore, the Swiss roll construction provides a solution for handling the output from the body opening. One zone can be made of a more resistant adhesive composition and another zone can be made of a skin friendly adhesive.

However the sealing effect of the zone, which comprises the more resistant adhesive composition of the Swiss roll construction, will not last for a longer period of time.

Hence, there is a need to find a solution to avoid leakage of bodily waste. Leakage may occur when the adhesive construction is destroyed. Destruction is typically caused by the acidic and aggressive output from the body opening.

It has now surprisingly been found that the collecting device according to the invention comprises a layered adhesive construction which provides a longer term solution for the leakage problem.

SUMMARY OF THE INVENTION

The present invention relates to a body waste collecting device comprising a collecting pouch and an adhesive wafer for attachment to the skin, said wafer comprising a backing layer and a first and second layer of hydrocolloid adhesive, where the second layer of hydrocolloid adhesive is at least partly interposed between the first layer of hydrocolloid adhesive and the backing layer, the first and second adhesive layers consisting of a continuous phase and a discontinuous phase, wherein
a) the discontinuous phase of the first adhesive layer comprises pectin, carboxymethyl cellulose, gelatine, guar gum, and potato starch,
b) the discontinuous phase of the second adhesive layer comprises carboxymethyl cellulose, gelatine, and guar gum,
c) the composition of the continuous phase of the first adhesive layer comprises a polyisobutylene, a styrene block copolymer, a butyl rubber, and a tackifier,
d) the composition of the continuous phase of the second adhesive layer consists of polyisobutylene and styrene block copolymer.

BRIEF DESCRIPTION OF THE DRAWING

The invention is disclosed more in detail with reference to the drawings, in which.

DETAILED DESCRIPTION OF THE INVENTION

Figure 1:
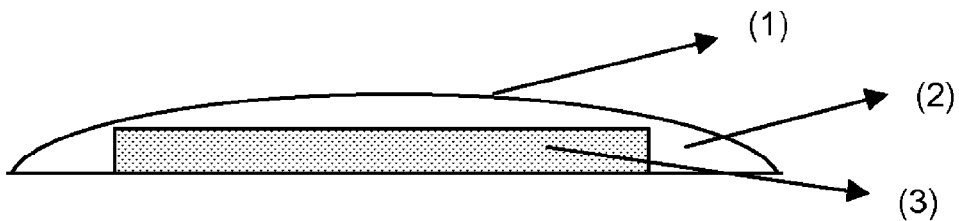
FIGS. 1-3 show different embodiments of the collecting device according to the invention.

The aim of the present invention is to provide a body waste collecting device, which improves the comfort of the patient and eliminates, or at least to a large extent, reduces the risk of skin irritation or skin damage in the area around the body opening of a patient.

One object of the invention is to provide a collecting device wherein the moisture from the body opening is prevented from passing through the adhesive construction.

By body waste collecting device is meant a device being able to collect and hold the output in a collecting item for a predefined time. The holding in place of the device may be obtained by a skin adhesive and the collecting may be obtained by a bag.

As used herein "discontinuous phase" means the hydrocolloid(s) or mixture of hydrocolloids and any other particulate solids in the adhesive layers, such as filler (native starch), colours etc.

As used herein "continuous phase" means the total adhesive composition except the discontinuous phase as defined above.

The Swiss roll construction provides a solution for handling the output from the body opening. The construction consists of alternating zones of adhesive material. One zone can be made of a more resistant adhesive composition and another zone can be made of a skin friendly adhesive. The zones are usually formed as co-axial rings or co-wound Archimedean spirals, which is illustrated in FIG. 9 of WO 89/05619. In this way the neighbouring zones are acting as a pair of two zones. The zone consisting of the more resistant adhesive composition can only last for a certain time before the aggressive output breaks through and immediately attacks the zone made of the skin friendly adhesive, which zone will last for a short time. The output has passed a pair of two zones and is ready to attack the next pair and the zone consisting of the more resistant adhesive composition. In this way the output of the body opening will be delayed in breaking through the device by the zones of the resistant adhesive composition. The speed of the breakthrough of the output depends on the resistance of the more resistant adhesive composition and the width and dimensions of the zones to pass. As the width of the zones is relatively small, the zones can only withhold for a certain time.

The layered adhesive construction of the collecting device according to the present invention provides a solution that can be used for a longer period of time.

The first adhesive layer according to the invention consists of a resistant adhesive composition.

The second adhesive layer consists of a skin friendly adhesive composition.

As in the Swiss roll construction, where the continuous phases of the two zones are different, the continuous phase of the first adhesive layer is different from the continuous phase of the second layer of adhesive according to the invention.

The composition of the continuous phase of the first adhesive layer according to the invention is different from the composition of the continuous phase of the second adhesive layer.

The Swiss role construction is made of separate zones in order to avoid migration of components of one zone to the neighbouring zone. Achieving the desired characteristics for the adhesive composition is a delicate matter. Migration of components may lead to change in characteristics of the adhesive in an unwanted manner.

In a layered adhesive construction, the two layers of adhesive have direct contact and migration can occur. It has now surprisingly been found that the components of the two adhesive layers of the device according to the invention do not migrate. Thus, the compositions of the two layers will maintain their different characteristics even in direct contact with the other adhesive composition in a layered construction.

According to a preferred embodiment of the invention, the composition of the continuous phase of the second adhesive layer consists of polyisobutylene and styrene block copolymer.

Skin friendly adhesive compositions comprising polyisobutylene and styrene block copolymer are disclosed in WO 2007/082538. The second layer of adhesive in the device according to the invention has similar skin friendly characteristics.

According to a preferred embodiment of the invention, the composition of the continuous phase of the first adhesive layer comprises a polyisobutylene, a styrene block copolymer, a butyl rubber, and a tackifier.

The components of styrene block copolymer and butyl rubber provide a better cohesion for the first layer of adhesive, thereby achieving an adhesive composition with increased resistance against aggressive output.

The presence of the tackifier in the composition of the first layer of adhesive improves the tack and the adhesiveness of this layer and the attachment of the device to the skin, thereby achieving an improved sealing effect against the aggressive output.

The combination of the two layers where the first adhesive layer, which is situated near the body opening and the output, has a high tack while preserving its integrity (high cohesion), provides a device with an adhesive construction, where the sealing effect against the aggressive output is improved, while the construction preserves its ability to take care of moisture from the skin and the characteristics of being skin friendly.

According to an embodiment of the invention, the continuous phase of the first adhesive layer comprises 40-50% w/w of polyisobutylene, 10-15% w/w styrene block copolymer, 15-20% w/w butyl rubber, and 25-30% w/w tackifier.

Preferably, the continuous phase of the second adhesive layer consists of a mixture of a polystyrene block copolymer and polyisobutylene.

According to a preferred embodiment of the invention, the continuous phase of the second adhesive layer consists of 15-25% w/w, preferably about 20% w/w, styrene block copolymer, such as Kraton D1107, Kraton D-1161 or similar styrene block copolymers and 75-85% w/w, preferably 80% w/w, liquid viscous polyisobutylene, such as Oppanol B 12 SFN.

Such compositions are described in U.S. Pat. No. 6,451,883.

The hydrocolloids used in the layers of the adhesive construction of the invention may be selected from natural, synthetic and semi-synthetic hydrocolloids. Hydrocolloids which are useful in adhesives are well known in the art. Suitable water soluble and water swellable hydrocollids include carboxymethyl cellulose (e.g. sodium carboxymetyl cellulose), pectin, gelatine, guar gum, locust bean gum, gum karaya, etc.

According to one embodiment of the invention, the discontinuous phase of the first adhesive layer comprises pectin, carboxymethyl cellulose, gelatine, guar gum and potato starch and the discontinuous phase in the second adhesive layer comprises carboxymethyl cellulose, gelatine and guar gum.

The first adhesive layer and the second adhesive layer of the device of the invention comprise a hydrocolloid, such as guar gum, providing a high gel strength to the adhesive when moisture is absorbed.

Preferably, the discontinuous phase of the first adhesive layer comprises 10-15% w/w of guar gum, 20-30% w/w pectin, and 15-30% w/w carboxymethyl cellulose (suitably sodium carboxymethyl cellulose).

In one embodiment of the invention, the discontinuous phase of the second adhesive layer comprises 35-45% w/w, preferably 40% w/w, of guar gum and 15-25% w/w, preferably 20% w/w, carboxymethyl cellulose (e.g. sodium carboxymethyl cellulose).

The hydrocolloids in the discontinuous phase of the first adhesive layer suitably comprise a mixture of:
10-15% w/w, preferably 13-14% w/w, of guar gum,
15-30% w/w, preferably 20-25% w/w, of carboxymethyl cellulose (e.g. sodium carboxymethyl cellulose)
20-30% w/w, preferably 25% w/w, pectin,
15-30% w/w, preferably 20-25% w/w, gelatine, and
10-20% w/w, preferably 14-17% w/w, potato starch based on the weight of the discontinuous phase.

The hydrocolloids in the discontinuous phase of the second adhesive layer suitably comprise a mixture of:
35-45% w/w, preferably 40% w/w, of guar gum,
15-25% w/w, preferably 20% w/w, carboxymethyl cellulose (e.g sodium carboxymethyl cellulose), and
35-45% w/w, preferably 40% w/w, gelatine based on the weight of the discontinuous phase.

The first adhesive layer suitably comprises 30-50% by weight of the discontinuous phase, preferably 40% of the discontinuous phase.

The second adhesive layer also suitably comprises 40-60% by weight of the discontinuous phase, preferably 50% of the discontinuous phase.

The first adhesive layer is preferably thicker than the second adhesive layer.

According to an embodiment of the invention, the first adhesive layer is thicker than the second adhesive layer, at least in the area where the second adhesive layer is interposed between the backing layer and the first adhesive layer.

In one embodiment of the invention the second adhesive layer is extending beyond the peripheral edge of the first adhesive layer and may contact the skin beyond the area where the first adhesive layer contacts the skin. According to this embodiment of the invention, the first adhesive layer may be embedded in the second adhesive layer. This embodiment of the invention is illustrated in FIG. 1 showing the backing layer (1), the second adhesive layer (2) and the first adhesive layer (3).

As used herein, "embedded" means that one layer is embedded in the other layer in such a way that (apart from the construction around the hole for the stoma) only one of the surfaces of embedded layer is not covered by the other layer. These adhesive constructions may be prepared as described in WO 00/18554.

Figure 2:
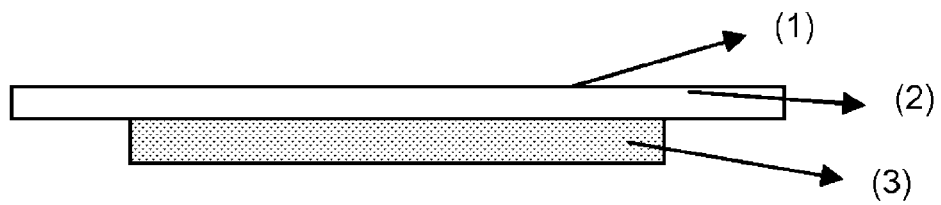

In another embodiment of the invention the second adhesive layer is attached on top of the first adhesive layer and the second adhesive layer extends beyond the peripheral edge of the first adhesive layer and may contact the skin beyond the area where the first adhesive layer contacts the skin. This is illustrated in FIG. 2 showing the backing layer (1), the second adhesive layer (2) and the first adhesive layer (3). Suitably, the first adhesive layer is thicker than the second adhesive layer.

Figure 3:
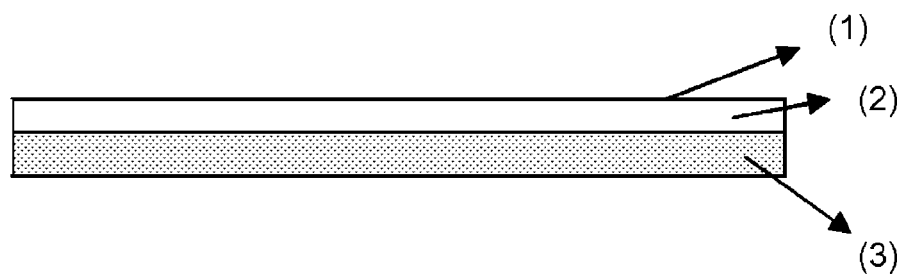

The first and second adhesive layer may have the same area and shape and be aligned on top of each other, see FIG. 3 showing the backing layer (1), the second adhesive layer (2) and the first adhesive layer (3). Again, the first adhesive layer is preferably thicker than the second adhesive layer. These adhesive constructions are prepared by preparing the layers separately and laminating the second adhesive layer between the backing layer and the first adhesive layer.

Suitably, the thickness of the first adhesive layer is 0.5-1 mm, preferably 0.5-0.9 mm, more preferred 0.5-0.8 mm, or more preferred 0.5-0.7 mm and the thickness of the second adhesive layer interposed between the backing layer and the first adhesive layer is suitably 0.1-0.4 mm, preferably 0.25-0.35 mm, or more preferred 0.3 mm.

The adhesive construction according to the invention may have bevelled peripheral edges where both adhesive layers are bevelled, or in case the second adhesive layer extends beyond the peripheral edges of the first adhesive layer, only the second adhesive layer is bevelled. This is illustrated in FIG. 1.

The surface of the adhesive layer (e.g. the second adhesive layer) attached to the backing layer is suitably covered completely by the backing layer.

The backing layer may be a thin polymeric film, a film having multiple polymeric layers, a non-woven fabric, or an open celled or closed celled foam layer optionally having its outer surface covered by a film.

Suitable material for thin polymeric films include polyolefins, such as polyethylene, polypropylene, ethylene acrylic acids, ethylene vinyl acetates, polyvinylchlorides, polyether sulfones, polyether ketones, polyurethanes, etc. The polymeric films are suitably impermeable to liquid water and may have a varying degree of water vapour permeability. Suitable non-woven fabrics include those made from polyester fibres, polypropylene fibres, nylon fibres, composite olefin fibres, or cellulose.

The thickness of the backing layer may vary depending on the material it is made of. The thickness of the backing layer is suitably 20-100 µm, preferably 40-70 µm.

The backing layer may also be a foam layer as described in U.S. Pat. No. 4,538,603. The backing layer may be of a weldable material so that other items or devices may be welded onto the backing layer.

The collecting pouch may be detachable from the adhesive wafer by a coupling system, or the pouch and the wafer may be integrated with the wafer, e.g. by welding. The two versions are known as one piece or two-piece appliances for ostomy.

According to an embodiment of the invention, the collecting device is an ostomy appliance. The ostomy appliance according to the invention may be a one piece or a two-piece appliance.

According to another embodiment of the invention, the collecting device is a faecal collecting device.

According to another embodiment of the invention, the collecting device is a fistula collecting device.

EXAMPLES

Materials

All percentages and parts given are weight/weight-% unless otherwise stated.

Oppanol B 12 SFN, a polyisobutylene from BASF, MW: 60.000-80.000
Kraton D-1161, a SIS block copolymer from KRATON Polymers
Butyl Rubber 101-3, from Lanxess
Arkon p90, a resin from Arakawa Europe
Akucell AF 2881, sodium carboxymethyl cellulose from AKZO
Gelatine UF 220 from PB Gelatins
Guar Gum FG-200 from Nordisk Gelatine
Pectin Pomosin LM 12 CG-Z/200 from Copenhagen Pectin
Potato starch M3 from Kartoffelmelcentralen.

Example 1

Composition of the second adhesive layer:

| Ingredient | Amount in gram |
| --- | --- |
| Oppanol B 12 SFN | 40 |
| Kraton D-1161 NU | 10 |
| Akucell AF 2881 | 10 |
| Gelatine UF 220 | 20 |
| Guar Gum FG-200 | 20 |

Example 2

Composition of the first adhesive layer:

| Ingredient | Amount in gram |
| --- | --- |
| Oppanol B 12 SFN | 27.0 |
| Kraton D-1161 | 6.5 |
| Butyl Rubber 101-3 | 10.5 |

-continued

| Ingredient | Amount in gram |
|---|---|
| Arkon p90 | 16.0 |
| Pectin Pomosin LM 12 CG-Z/200 | 10.0 |
| Akucell AF 2881 | 9.5 |
| Gelatine PB 220 | 8.75 |
| Potato starch | 6.25 |

Example 3

The hydrocolloid adhesives may be prepared by heating the ingredients in a Z-mixer according to methods well known in the art, and the layered adhesive construction may be prepared according to the method described in WO 00/18554.

The invention claimed is:

1. A body waste collecting device comprising a collecting pouch and an adhesive wafer for attachment to the skin, said wafer comprising a backing layer and a first and second layer of hydrocolloid adhesive, where the second layer of hydrocolloid adhesive is at least partly interposed between the first layer of hydrocolloid adhesive and the backing layer, the first and second adhesive layers consisting of a continuous phase and a discontinuous phase, wherein
   a) the discontinuous phase of the first adhesive layer comprises pectin, carboxymethyl cellulose, gelatine, guar gum, and potato starch,
   b) the discontinuous phase of the second adhesive layer comprises carboxymethyl cellulose, gelatine, and guar gum,
   c) the composition of the continuous phase of the first adhesive layer comprises a polyisobutylene, a styrene block copolymer, a butyl rubber, and a tackifier,
   d) the composition of the continuous phase of the second adhesive layer consists of polyisobutylene and styrene block copolymer.

2. The collecting device according to claim 1, wherein the discontinuous phase of the first adhesive layer comprises 10-15% w/w of guar gum, 20-30% w/w pectin, and 15-30% w/w carboxymethyl cellulose.

3. The collecting device according to claim 1, wherein the discontinuous phase. of the second adhesive layer comprises 35-45% w/w of guar gum, and 15-25% w/w carboxymethyl cellulose.

4. The collecting device according to claim 1, wherein the continuous phase of the first adhesive layer comprises 40-50% w/w of polyisobutylene, 10-15% w/w styrene block copolymer, 15-20% w/w butyl rubber, and 25-30% w/w tackifier.

5. The collecting device according to claim 1, wherein the continuous phase of the second adhesive layer consists of between 75 and 85% w/w of polyisobutylene and 15-25% w/w styrene block copolymer.

6. The collecting device according to claim 1, wherein the first adhesive layer comprises 30-50% by weight of the discontinuous phase.

7. The collecting device according to claim 1, wherein the second adhesive layer comprises 40-60% by weight of the discontinuous phase.

8. The collecting device according to claim 1, wherein the first adhesive layer is thicker than the second adhesive layer at least in the area where the second adhesive layer is interposed between the backing layer and the first adhesive layer.

9. The collecting device according to claim 1, wherein the second adhesive layer extends beyond the peripheral edge of the first adhesive layer.

10. The collecting device according to claim 1, wherein the first adhesive layer is embedded in the second adhesive layer.

11. The collecting device according to claim 1, wherein the collecting device is an ostomy appliance.

* * * * *